United States Patent [19]

Anthony et al.

[11] Patent Number: 5,177,045

[45] Date of Patent: Jan. 5, 1993

[54] CRYSTALLINE TITANATE CATALYST SUPPORTS

[75] Inventors: Rayford G. Anthony, Bryan, Tex.; Robert G. Dosch, Albuquerque, N. Mex.

[73] Assignee: The United States of America as represented by the United States Department of Energy, Washington, D.C.

[21] Appl. No.: 751,003

[22] Filed: Aug. 28, 1991

[51] Int. Cl.$^5$ ............................................. B01J 31/12
[52] U.S. Cl. .................................... 502/164; 502/170; 502/344; 502/350; 502/220; 502/221; 502/309; 502/330
[58] Field of Search ............... 502/164, 170, 344, 350, 502/220, 221, 309, 330

[56] References Cited

U.S. PATENT DOCUMENTS

| | | | |
|---|---|---|---|
| 4,061,583 | 12/1977 | Murata et al. | 252/62.3 BT |
| 4,511,455 | 4/1985 | Dosch et al. | 208/10 |
| 4,636,378 | 1/1987 | Pastor et al. | 423/598 |
| 4,696,810 | 9/1987 | Shirasaki et al. | 423/593 |
| 4,832,939 | 5/1989 | Menashi et al. | 423/598 |
| 4,946,810 | 8/1990 | Heistand, II et al. | 501/137 |
| 4,957,888 | 9/1990 | Brand et al. | 501/134 |
| 5,008,094 | 4/1991 | Keijsper et al. | 502/77 |

OTHER PUBLICATIONS

A. Clearfield et al., "Preparation, Structure, and Ion-Exchange Properties of $Na_4Ti_9O_{20}.xH_2O$", *Journal of Solid State Chemistry*, vol. 73, 1988, pp. 98–106.

J. Lehto, "Sodium Titanate for Solidification of Radioactive Wastes Preparation, Structure and Ion Exchange Properties", Report Series in Radiochemistry, May 1987, University of Helsinki.

R. Dosch et al., "Hydrous Metal Oxide-Supported Catalysts: Part I, Preparation Chemistry and Physical and Chemical Properties", SAND89-2399, Feb. 1990.

R. Dosch et al., "Hydrous Metal Oxide-Supported Catalysts: Part II, Catalytic Properties and Applications", SAND89-2400, Feb. 1990.

H. Stephens et al., "Hydrous Metal Oxide Ion Exchangers for Preparation of Catalysts for Direct Coal Liquefaction", *Industrial & Engineering Chemistry Product Research and Development*, vol. 24, No. 1, 1985, pp. 15–19.

K. Gruber, "The Selective Catalytic Reduction of Nitric Oxide With Ammonia in the Presence of Oxygen", M. S. Thesis, Chemical Engineering Department, Texas A&M University, Aug. 1989.

*Primary Examiner*—Patrick P. Garvin
*Assistant Examiner*—Brent M. Pebbles
*Attorney, Agent, or Firm*—Armand McMillan; James H. Chafin; William R. Moser

[57] ABSTRACT

A series of new crystalline titanates (CT) are shown to have considerable potential as catalyst supports. For Pd supported catalyst, the catalytic activity for pyrene hydrogenation was substantially different depending on the type of CT, and one was substantially more active than Pd on hydrous titanium oxide (HTO). For 1-hexene hydrogenation the activities of the new CTs were approximately the same as for the hydrous metal oxide supports.

34 Claims, 5 Drawing Sheets

CRYSTALLINE TITANATE CATALYST SUPPORTS

The Government has rights in this invention pursuant to Contract No. DE-AC04-76DP00789 between the U.S. Department of Energy and AT&T Technology.

BACKGROUND OF THE INVENTION

1. Field of the Invention

The present invention relates generally to a crystalline titanate catalyst support having a layered structure. In particular, this invention relates to a catalyst support which has high ion-exchange properties, high surface areas and high hydrogenation activity relative to hydrous titanium oxide supports.

2. Description of the Related Art

Hydrous titanium oxides (HTO) are known to be excellent supports for Co, Mo, Ni, Pd, or vanadia for hydrogenation and oxidation reactions. See Stephens H. P. et al., Ind. & Engr. Chem. Prod. Res. & Dev., Vol. 24, pages 15–19 (1985). Specifically, Dosch et al. have used ion exchange techniques to prepare Co-HTO, Mo/Ni-HTO, and Pd-HTO for use as Fischer-Tropsch catalysts and coal liquefaction catalysts. See "Hydrous Metal Oxide-Supported Catalysts: Part I. A Review of Preparation Chemistry and Physical and Chemical Properties", SAND89-2399, Sandia National Laboratories (1990) and "Hydrous Metal Oxide-Supported Catalysts: Part II. A Review of Catalytic Properties and Applications", SAND89-2400, Sandia National Laboratories (1990). See also U.S. Pat. No. 4,511,455. Gruber, K. A., "The Selective Catalytic Reduction of Nitric Oxide With Ammonia in the Presence of Oxygen", M. S. Thesis, Chem. Eng. Dept. Texas A&M University, (August, 1989) used HTO as a support for vanadia in the selective catalytic reduction of nitric oxide with ammonia in the presence of oxygen.

HTO based catalysts are known to provide high activities and surface areas. However, one of the drawbacks of using HTO materials as catalyst supports in high-temperature applications is the change in activity which occurs as the material proceeds through the amorphous to crystalline transition usually to anatase titania. This phase conversion generally results in a decrease in surface area, and very dense material. The phase conversion accelerates as temperature increases, which minimizes the number of practical applications for crystalline HTO. For example, coal liquefaction reactions require a temperature between 300° and 500° C.

U.S. Pat. No. 4,696,810 (Shirasaki et al.) discloses metal titanates prepared by high temperature reactions between oxides such as BaO and TiO. The metal titanates in Shirasaki et al. do not have a layered structure, are typically refractory, have surface areas below 10 $m^2/g$, and poor ion exchange properties (less than 1 milliequivalent per gram). The possibility of preparing crystalline titanate compounds that do not undergo a phase transition would thus be desirable.

SUMMARY OF THE INVENTION

Therefore, one object of the present invention is to produce crystalline titanates for catalytic supports which overcome the aforementioned problems of the related art, particularly, crystalline titanates which possess high activity at high temperatures.

It is another object of the present invention to prepare crystalline titanates which have high ion exchange properties.

A further object of the present invention is to prepare crystalline titanates which have high surface areas.

A further object of the present invention is to prepare crystalline titanates which have a higher activity than hydrous titanium oxide catalysts.

Another object of the present invention is to prepare crystalline titanates having a layered structure and an interlayer distance (d-spacing) above 1.0 nm.

The present invention provides a process for forming a crystalline catalyst support having a layered structure comprising mixing a titanium-containing compound with an alkali metal hydroxide, a tetraalkylammonium halide, and a tetramethylammonium hydroxide at a temperature above 25° C.

The present invention also provides a crystalline catalyst support formed according to the process described above.

The present invention also provides a method of using such a catalyst support by contacting the support with an unsaturated hydrocarbon and hydrogenating the unsaturated hydrocarbon.

The present invention also provides a process comprising mixing a titanium-containing compound and an alkali metal hydroxide at a temperature above room temperature (about 25° C.), thereby forming a crystalline titanate having a d-spacing of about 1.0 nm and a surface area of about 160 $m^2/g$.

By following a process of the present invention, a crystalline catalyst support having a surface area between 50 and 200 $m^2/g$ and a d-spacing of at least 1 nm can be produced. The resulting crystalline titanates have high activities and excellent ion exchange properties.

BRIEF DESCRIPTION OF THE DRAWINGS

These and other advantages and objects of the invention will become apparent to one of ordinary skill in the art with reference to the following description and the accompanying drawings, wherein.

DETAILED DESCRIPTION OF THE PREFERRED EMBODIMENTS

The present invention provides a process for forming a crystalline catalyst support having a layered structure comprising mixing a titanium-containing compound with an alkali metal hydroxide, a tetraalkylammonium halide, and a tetramethylammonium hydroxide at a temperature above room temperature (about 25° C.).

Suitable titanium-containing compounds according to the present invention include tetraisopropyl titanate, titanium oxides, titanium alkoxide, and titanium halides.

Other suitable ingredients for crystalline titanates in accordance with the invention, and their preferred proportions, are described below. The proportions of each ingredient are based on the number of moles of the ingredient per mole of titanium.

Suitable alkali metal hydroxides include sodium hydroxide, potassium hydroxide, and other alkali salts. The alkali metal hydroxide is preferably provided in an amount within the range of from about 0.2 to about 6 moles per mole of titanium, more preferably about 0.5–1.5 moles per mole of titanium.

Suitable tetraalkylammonium halides include tetrapropylammonium bromide, tetrabutylammonium bromide, tetrapropylammonium chloride and tetrapentylammonium chloride.

Suitable tetraalkylammonium hydroxides include tetramethylammonium hydroxide, tetrapropyl ammonium hydroxide, tetrapentol and tetrahexol. The tetramethylammonium hydroxide is preferably provided in an amount within the range of from about 0 to about 6 moles per mole of titanium, more preferably about 1–1.5 moles per mole of titanium. Tetrapropylammonium halide is preferably provided in an amount of from about 0.25 to about 0.37 mole per mole of titanium, more preferably from about 0.25 mole per mole of titanium.

The crystalline titanates supports may optionally be loaded with either metals or metal oxides. Suitable metals include aluminum, palladium, nickel, molybdenum, nickel sulfide, molybdenum sulfide and any other di- and trivalent metals and metal oxides. Palladium is preferably provided in an amount within the range of 0.1 to 1.0 mole per mole of titanium. Suitable sources for aluminum include aluminum nitrate, aluminum alkoxides, aluminum chloride, aluminum isopropoxide and aluminum suboxide. Aluminum is preferably provided in an amount within the range of from about 0.05 to about 0.1 mole per mole of titanium. Suitable metal oxides include molybdenum oxide and cobalt oxide.

The catalyst supports may optionally be acidified either before or after loading with a metal or metal oxide. Preferred acids include $H_2SO_4$, HCl and organic acids.

A specifically preferred crystalline titanate according to this invention has molar proportions of $NaOH:R_4NH^+ {}_4OH-:Al:R_4NH^+ {}_4X:H_2O:CH_3OH:Ti$ of 0.5:0.5:0.5:0.25:21:4.5:1, where R equals an alkyl group.

Prior to this invention, tetramethylammonium hydroxide would not be used as part of the alkali material for synthesizing amorphous titanates. It is known that tetramethylammonium hydroxide typically gels during processing of amorphous titanates and hence it would not have been considered suitable for manufacturing titanate catalysts. The inventors have provided a method for implementing tetramethylammonium hydroxide in a process for forming crystalline titanate catalyst supports.

The general characteristics of six specifically preferred embodiments will now be described. For simplicity, these six embodiments are called Type 1, Type 2, Type 3, Type 4a, Type 4b and Type 5. The preparation of these embodiments is described below (Examples 1–6).

Figure 1:
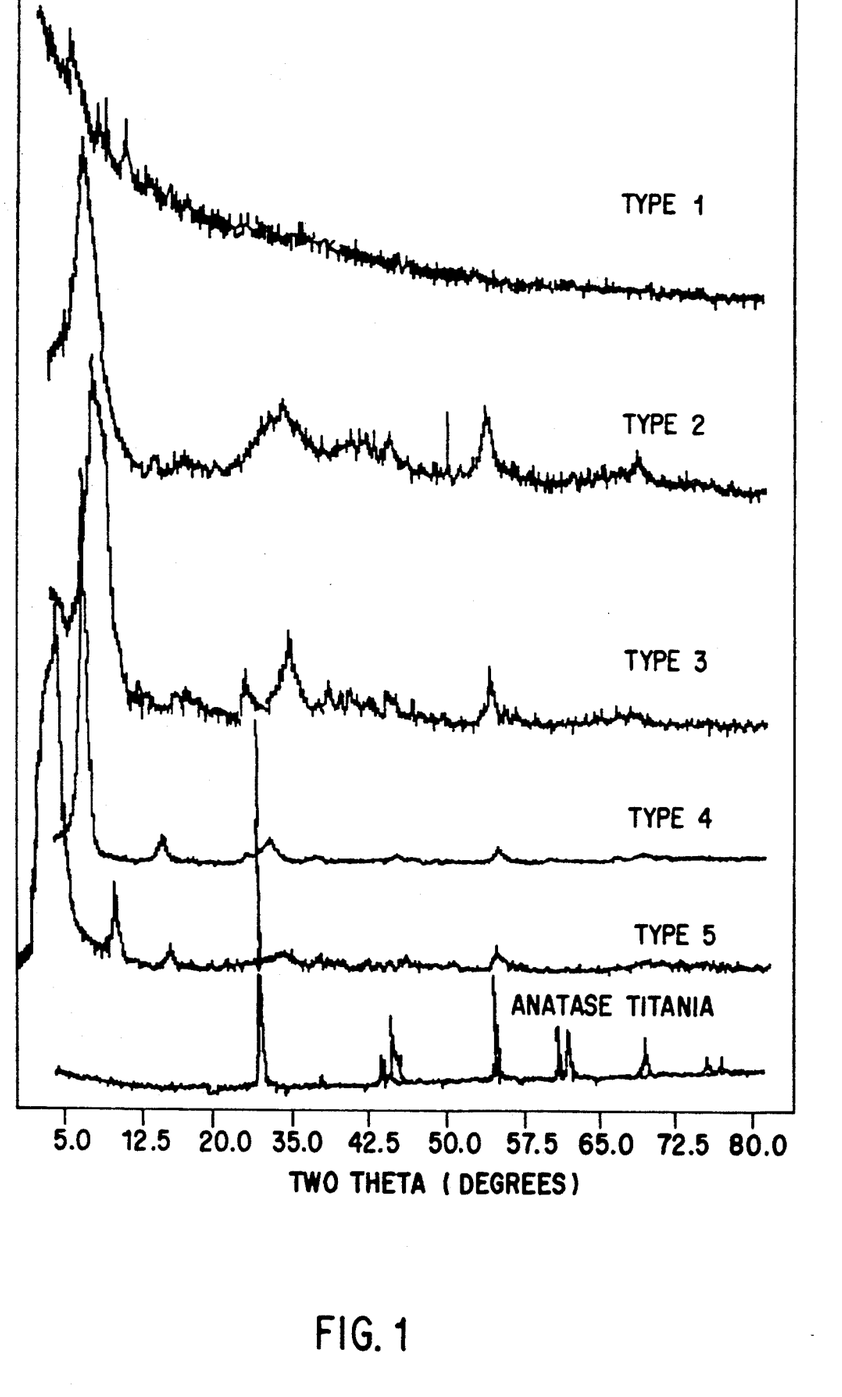
FIG. 1 shows X-ray diffraction patterns of the crystalline titanates of the invention and the X-ray diffraction pattern of Anatase Titania.
Figure 2A:
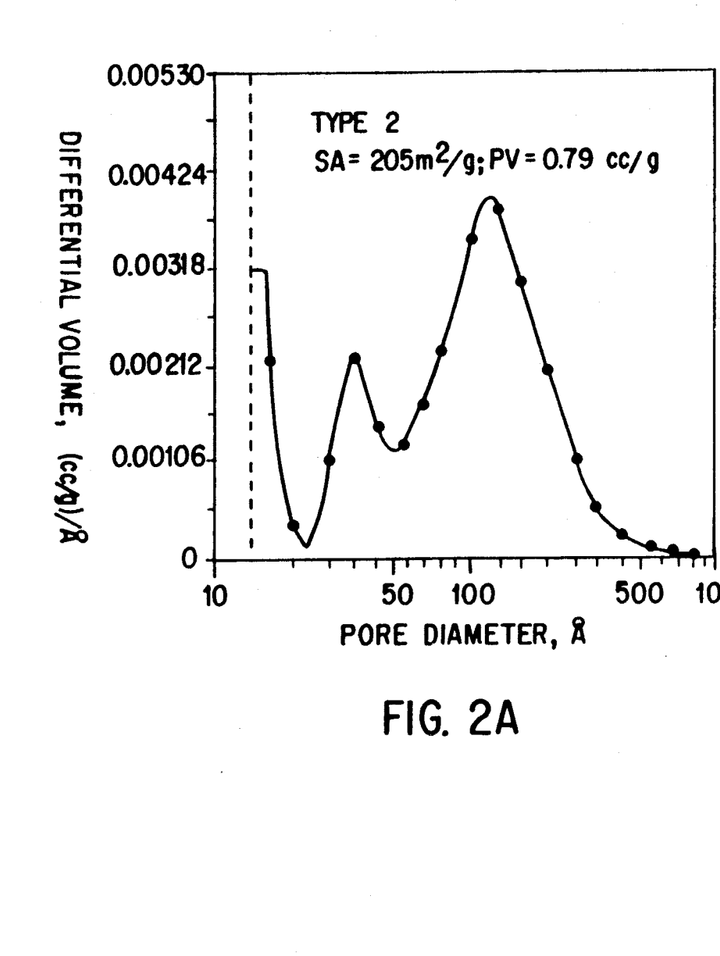
FIGS. 2A–2D are plots of differential volume against pore diameter of the preferred crystalline titanates.
Figure 2B:
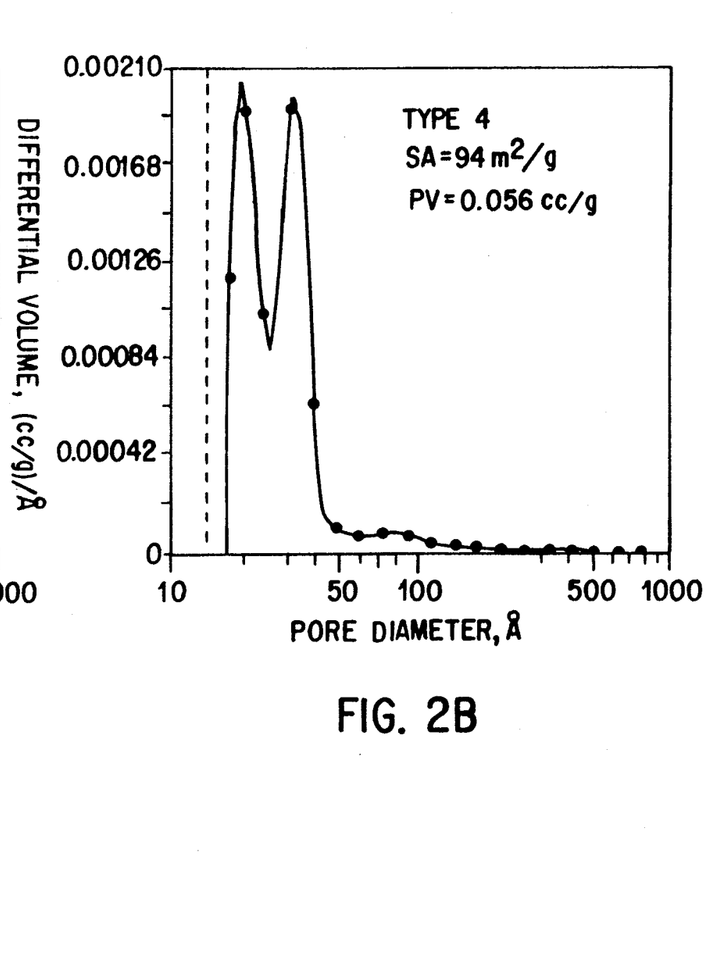
Figure 2C:
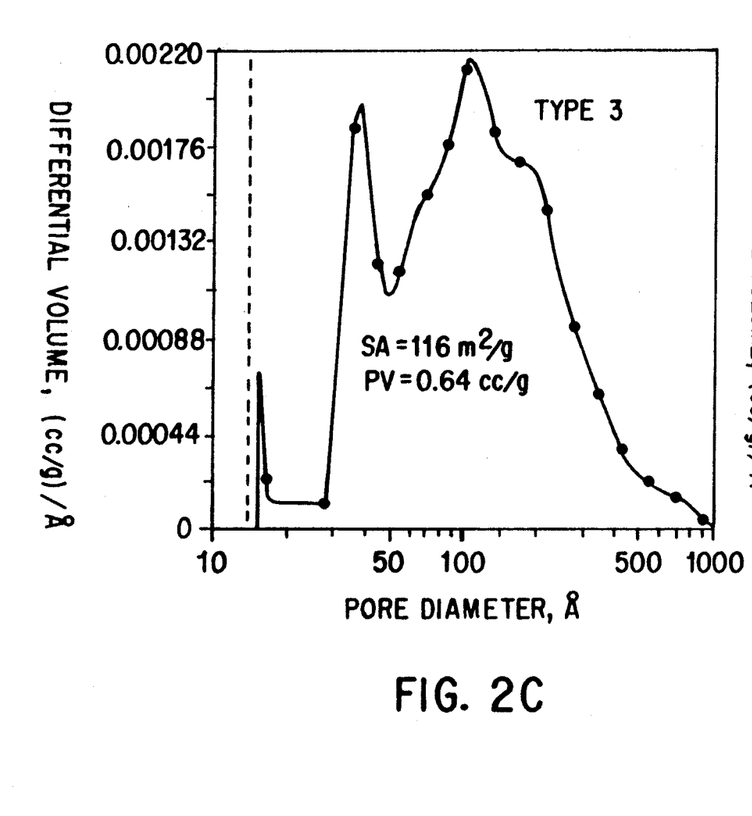
Figure 2D:
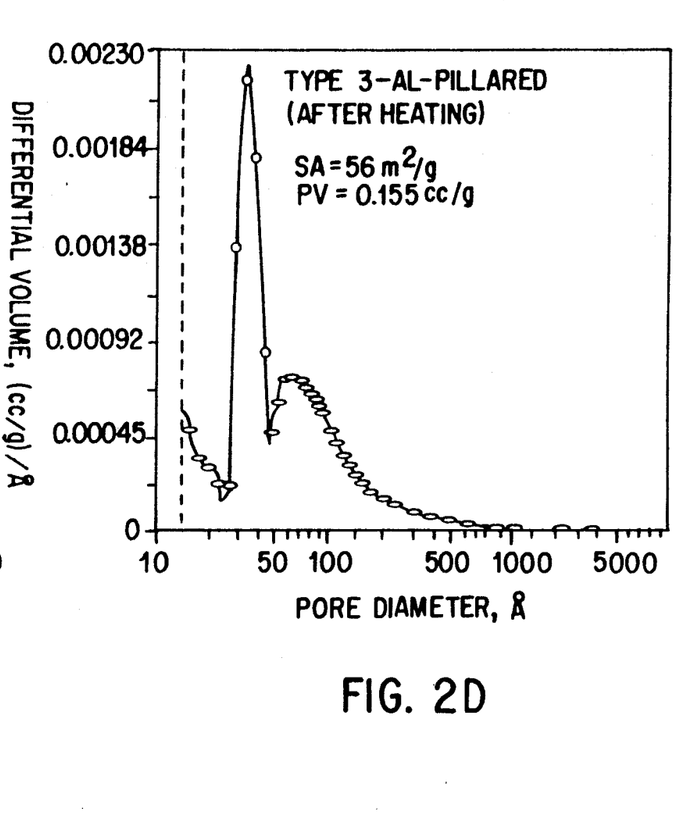

The Type 1 titanate has a first reflection at a d-spacing of approximately 1.0 nm. The X-ray diffraction pattern of the Type 1 titanate suggests a poorly crystalline material, but upon examination under an optical microscope, the crystals were easily observable and had a needle-type morphology. Type 1 titanates equilibrated in solutions containing a two-fold or more excess of $H^+$, Ni(II), or V(V) ions (based on the ion exchange capacity), were found to have surface areas of 377, 373, and 232 $m^2/g$, respectively, and pore volumes of 0.52, 0.42, and 0.43 g/cc, respectively, after outgassing at 300° C. Under similar conditions, sodium hydrous titanium oxide has a surface area of 41 $m^2/g$ and pore volume of 0.14 cc/g. In addition, the pore size distributions for these exchanged samples were bimodal and trimodal as shown by FIGS. 2A–2C, whereas hydrous sodium titanium oxide (HTO) is unimodal. The Type 2 titanate contains aluminum from nitrates, alkoxides, and chlorides of aluminum. Type 2 titanates have d-spacings of approximately 1.0 nm of the first reflection, however the remaining portions of the X-ray diffraction patterns are slightly different. Type 2 titanates have a pore volume of 0.79 cc/g, pore sizes up to 50 nm, and are bimodal with peaks at about 5 nm and 10 nm. The surface area of Type 2 titanates is almost twice the surface areas of the Type 3, 4, and 5 titanates.

More preferably, the Type 2 titanates may be formed without tetraalkylammonium halide and with sodium hydroxide, rather than quaternary ammonium hydroxide. Since these quaternary ammonium ingredients are expensive, their exclusion in the Type 2 titanates is highly advantageous.

Type 3 contains only titanium, sodium, organic cations, and oxygen. Type 3 can be prepared from the amorphous hydrous titanium oxide.

The next group of titanates were classified as Types 4a and 4b because of the differences in surface areas, reactivity, and synthesis conditions. The d-spacing of the first reflection of Type 4 titanates was 1.17 nm and the rest of the patterns were essentially identical.

The Type 4 titanates (d-spacing = 1.17 nm) have surface areas of 94 to 133 $m^2/g$ and bimodal distributions (FIG. 2). Type 4 pore sizes are in the range of 1.8 to 5.0 nm, and show peaks at 2 and 4 nm. Pore volumes of Type 4 samples are low, about 0.069 and 0.065 cc/g. The low pore volumes indicate that the space between each layer is filled. Elemental analysis and a carbon balance indicate that a mixture of tetramethylammonium and tetrapropylammonium cations occupy the space between the layers with 25% tetrapropyl ammonium and 75% tetramethyl ammonium ions.

The Type 5 titanate had a d-spacing of 1.6 nm, although the material showed a mixture of anatase and the new layered titanate when heated at 180° C. Type 5 may be obtained without any anatase if its components are heated at 125° C. for 8 hours. In obtaining this pure form of Type 5, it is important to store the solution at room temperature overnight prior to heating.

The activities of crystalline titanate supported catalysts may be analyzed by hydrogenating an unsaturated hydrocarbon. Preferably the unsaturated hydrocarbon is pyrene.

In one embodiment, Types 1, 2, 3, and 4 were ion exchanged with a $PdCl_2$ solution to obtain a Pd loading of approximately 1%. As prepared solutions (AP) had a final pH greater than 10. After filtering and drying, the catalysts were acidified (AC.) with sulfuric acid to a pH of 3.5 to 4. Pd was also loaded onto anatase, amorphous titanium oxides, $Na_{0.5}T$, $Na_{0.3}T$, and an amorphous titanium silicon oxide, $Na_{0.5}T$—Si.

The catalytic activity of standard catalysts was tested for comparison with the activity of preferred crystalline titanates of the invention. Catalytic activity was evaluated by the rate of pyrene hydrogenation using zero-order rate constants k. Catalytic activity was also evaluated by the rate of 1-hexene hydrogenation, using a first order rate constant. The results of these activity measurements are reported in Table 1.

TABLE 1

Evaluation of Catalytic Activity at 100° C. and 100 psig at 22° C.

| Sample | Pd in CT. Wt. % | K(pyrene)[1] mg/(g s) | K(1-hexene)[3] 1/(g s) |
|---|---|---|---|
| CT TP1 AC[2] | 0.74 | 380 | — |
| CT TP2 AC | 0.78 | 610 | — |
| CT TP3 AC | 1.36 | 348 | 59 |
| CT TP4a AC | 0.87 | 82 | — |
| CT TP4b AC | 0.56 | 24 | 34 |
| CT TP4b AP[4] | 0.55 | 15 | 46 |
| Anatase AC | 0.83 | 170 | — |
| Na$_{0.5}$ T AC | 0.63 | 199 | 56 |
| Na$_{0.3}$ T AC | 0.53 | 329 | — |
| Na$_{0.5}$T-Si(Pd#3) | 0.55 | 577 | — |

[1] Crystalline Titanate mg of pyrene hydrogenated/(second gram of Pd).
[2] Acidified after preparing. Non-acidified catalysts were significantly less active than the acidified catalyst. TP1 is Type 1 titanate.
[3] First order rate constant for hexene hydrogenation, 1/(second gram of Pd).
[4] As prepared prior to acidification.

All of the preferred crystalline titanate catalysts, except for the Type 4 acidified (CT TP4 a and b AC), show activities greater than the Pd-HTO catalysts (i.e., Na$_{0.5}$T AC and Na$_{0.3}$ T AC). Type 2 acidified (CT TP2 AC) had an activity more than twice that of the Na$_{0.5}$T AC and almost twice the activity of the Na$_{0.5}$T AC. The reason for the superior activity of the Type 2 titanate (CT TP2 Ac) is unknown, but it is speculated that it may be due to the ordering introduced by crystallization of the support, or to the presence of aluminum.

The rate of hydrogenation of 1-hexene for hydrous titanium oxides was compared to the same rate of hydrogenation for Type 2 and Type 4b crystalline titanates. The results are shown in TABLE 2.

TABLE 2

Hydrogenation of 1-Hexene[1]

| Product Gas Chromatography Retention Time | neat 1-hexene | neat n-hexene[2] blank run with cat. | 1-hexene blank run no cat. | PD-HTO AP | Pd-HTO ACID | TYPE 2 AP | TYPE 2 ACID | TYPE 4b AP | TYPE 4b ACID |
|---|---|---|---|---|---|---|---|---|---|
| 4.42-.48 | 99.72 | — | 95.0 | 17.1 | 2.31 | 19.40 | 1.57 | 10.58 | 17.95 |
| 4.69-.74 | 0.04 | 99.6 | 3.40 | 28.8 | 28.33 | 26.96 | 29.11 | 27.55 | 30.13 |
| 4.77-.78 | 0.24 | — | 0.24 | 0.20 | 0.16 | 0.21 | 0.12 | 0.17 | 0.19 |
| 4.88-.89 | — | — | 0.15 | 2.09 | 8.61 | 2.00 | 9.33 | 7.65 | 4.33 |
| 4.96-.98 | — | — | — | 34.44 | 41.37 | 33.11 | 42.39 | 36.19 | 29.97 |
| 5.22-.24 | — | — | 1.24 | 17.36 | 19.22 | 18.49 | 17.36 | 17.81 | 17.38 |
| 5.42-.46 | — | 0.39 | 0.02 | 0.02 | 0.06 | 0.02 | 0.09 | 0.05 | 0.04 |
| Catalyst Weight, mg | NA | 12.4 | NA | 10.2 | 10.7 | 10.5 | 10.1 | 9.8 | 9.9 |
| Catalyst Pd content % | NA | 0.70 | NA | 0.74 | 0.70 | 0.73 | 0.78 | 0.55 | 0.56 |
| Pyrene[3] Hydrog. Rate, R | NA | 524 | NA | 85 | 524 | 74 | 610 | 15 | 24 |

[1] All runs made at 100° C. for 15 min under 100 psig H$_2$ cold charge using 0.5 g of 1-hexene (or n-hexene in the case of the one blank run). Data given in % of total area accounts for 1-hexene plus all reaction products. Selectivity factors for all species were assumed to be the same.
[2] The PD-HTO-ACID catalyst was used in this run.
[3] mg pyrene hydrogenated/sec · g PD A summary of the properties of the Type 1-5 crystalline titanates, as prepared and as acidified, are listed below. Also listed are the properties of well known Pd catalysts for comparison purposes.

TABLE 3

Catalytic Properties of Pd Catalysts Prepared On Five Different Types of New Crystalline Titanates

| Catalyst | pH | Pd. wt % | k |
|---|---|---|---|
| TYPE 1 AP | 11.53 | 0.70 | 31 |
| TYPE 1 AC | 3.71 | 0.74 | 380 |
| TYPE 2 AP | 10.27 | 0.73 | 74 |
| TYPE 2 AC | 3.71 | 0.78 | 610 |
| TYPE 3 AP | 11.12 | 1.15 | 86 |
| TYPE 3 AC | 3.68 | 1.36 | 348 |
| TYPE 4a AP | 5.77 | 0.89 | 32 |
| TYPE 4a AC | 3.85 | 0.87 | 82 |
| TYPE 4b AP | 7.34 | 0.89 | 7 |
| TYPE 4b AC | 3.61 | 0.71 | 6 |
| TYPE 5 AP | 8.00 | 1.31 | 0 |
| TYPE 5 AC | 3.00 | 1.32 | 32 |
| Na$_{0.5}$T AP | 10.00 | 0.61 | — |
| NA$_{0.5}$T AC | 3.76 | 0.63 | 199 |
| Na$_{0.3}$T AP | 9.15 | 0.53 | 204 |
| Na$_{0.3}$T AC | 3.91 | 0.53 | 329 |
| Anatase AP | 4.80 | 0.87 | 170 |
| Anatase AC | 3.69 | 0.83 | 170 |
| Pd#2 | 3.60 | 0.70 | 524 |
| Pd#3 | 2.40 | 0.55 | 577 |

The source areas and pore size distributions of crystalline titanate catalysts can be characterized by using X-ray diffraction, BET Analysis, Scanning Electron Micrograph, Raman and Infra-red spectroscopy. The catalysts can also be subjected to thermogravimetric analysis, differential scanning calorimetry and atomic absorption studies for further characterization. The results of the different analyses performed on the preferred crystalline titanates indicate significant differences between the crystalline titanates and the hydrous titanium oxides from which they were derived. These results are briefly summarized below.

Thermogravimetric Analysis and Differential Scanning Colorimetry

Thermogravimetric (TGA) and differential scanning calorimetry (DSC.) studies were performed on the Type 4 titanates. Heating rates for the TGA studies were 5°/min and 10°/min for the DSC experiments. An initial weight loss of approximately 5 to 8%, occurred below 100° C., and is probably due to loss of water. Very little weight loss occurred up to 200° C. and then a fairly rapid loss of weight occurred up to a temperature of 400° C. The TGA in air and nitrogen differ slightly but show the same general trend. Total weight loss is approximately 18 to 20% in nitrogen and air, respectively.

The DSC's were conducted at 10° C./min in the presence of nitrogen and air. A strong exotherm occurred in air over the temperature range of 240 to 360° C., which is probably due to the combustion of the organic template. A second exotherm occurred with a peak of 450° C., which was probably due to a phase transformation. In nitrogen, no reaction appeared to occur except for a peak at 400° C. which is probably due to a phase transformation. Surprisingly, no endotherm occurred due to the pyrolysis of the organic template.

BET Analysis

The surface areas and pore size distributions of samples (FIG. 2) were determined by BET using a Micrometrics Digisorb 2600. The samples were degassed at 150° C. prior to the nitrogen sorption experiments. Typical sorption curves for layered materials were obtained.

Infrared and Raman Spectra

Figure 3A:
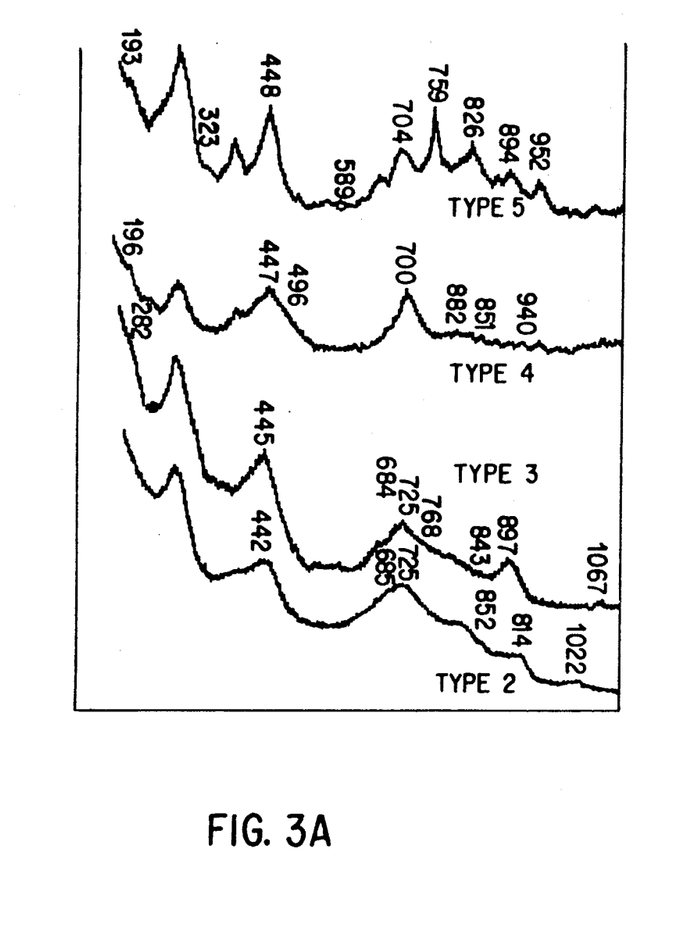
FIG. 3A shows the raman spectra of representative crystalline titanates of the invention.
Figure 3B:
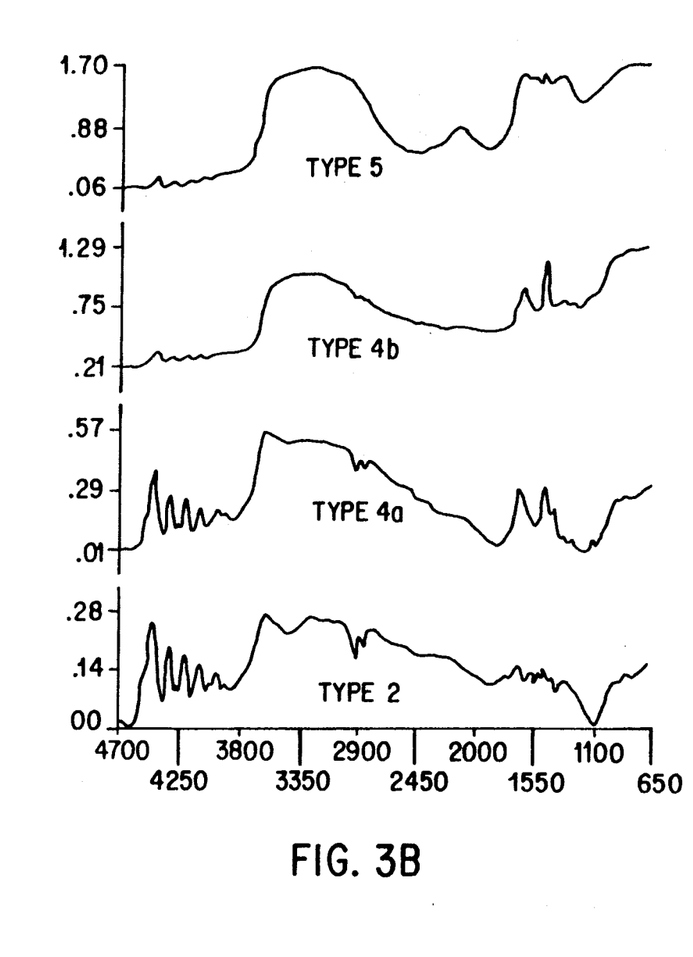
FIG. 3B shows the infrared spectra of representative crystalline titanates of the invention.

Infrared and Raman spectra were obtained on selected samples of the new titanates. The IR spectra illustrate the incorporation of the tetraalkylammonia cation. Somewhat surprising was that some spectra did not have bands in the 3,900–4,500 cm region, which would be typical of a quaternary ammonium compound. Also, the spectra substantiate the differences in the five types of new titanates. FIGS. 3 illustrates typical spectra obtained in these studies.

Pillaring

Titanate Types 2-5 were ion exchanged with a solution of aluminum ions produced by dissolution of "microdry" (aluminum chlorohydrate available from the Rhesus Chemical Company). The solution contained cations of $(AL_{13}O_4(OH)_{24}*12\ H_2O)^{7+}$, the aluminum Keggin ion. The exchange was conducted for two hours and the pH controlled to 4.9 The amounts of aluminum exchanged into the crystalline titanates is given in Table 4.

TABLE 4

| Extent of Ion Exchange | | | | |
| --- | --- | --- | --- | --- |
| Type | 2 | 3 | 4 | 5 |
| Wt % Al | 2.1 | 16.8 | 4.8 | 17.4 |

X-Ray Diffraction

Figure 4:
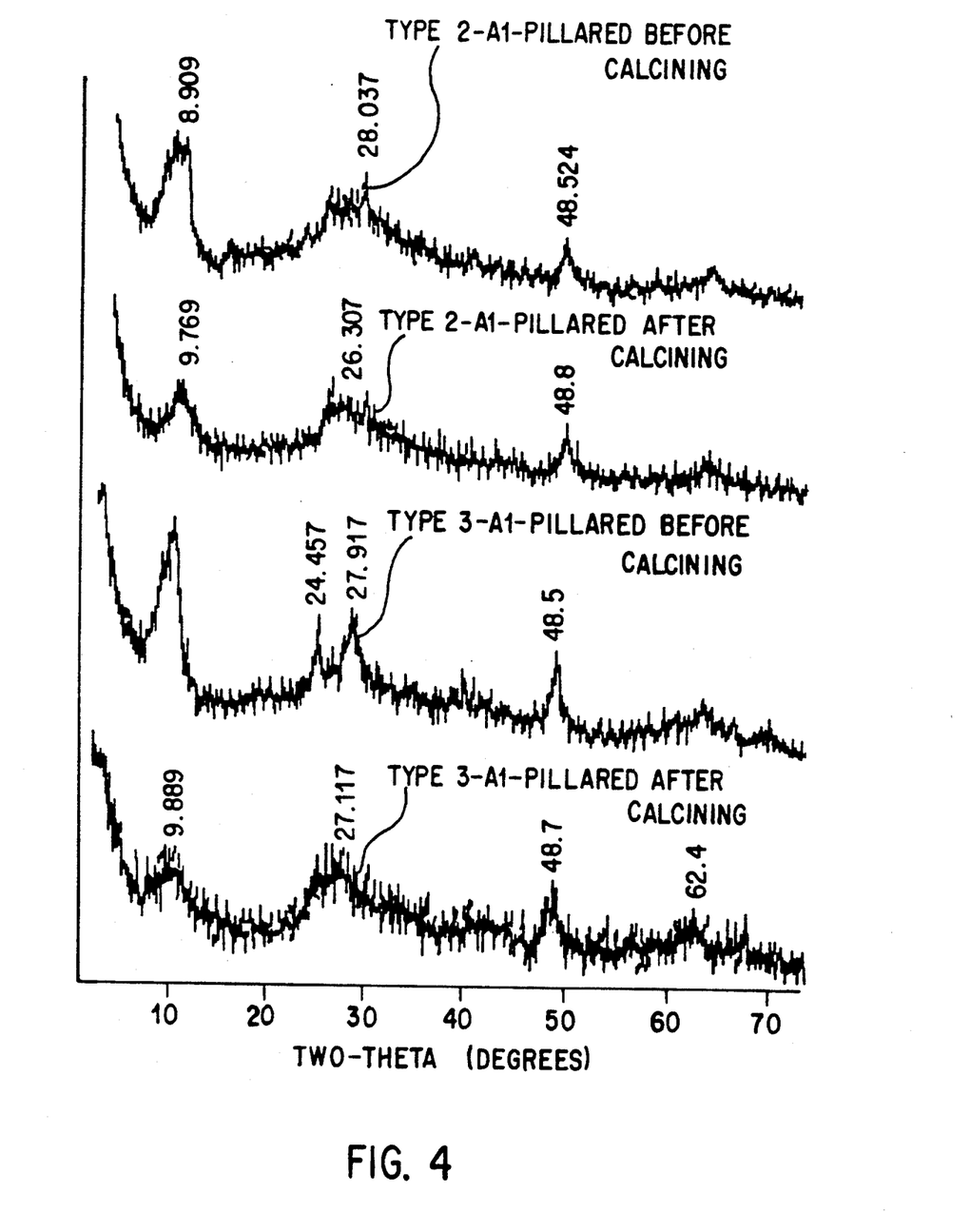
FIG. 4 X-ray diffraction patterns for aluminum pillared crystalline titanate before and after calcining.

X-ray diffraction patterns were obtained on the resulting samples before and after calcining at 300° C. for 1 hour. The X-ray diffraction RD patterns (FIG. 4) for Types 2 and 3 show that the layered structure is retained after ion exchange and heating. The d-spacings after heating were 0.99 and 0.94. Anatase was formed from Types 4 and 5 titanates, after calcining. Prior to the incorporation of the aluminum Keggin ion, the crystalline titanates became amorphous between 200° and 300° C., and on further heating anatase is formed. FIG. 2 shows the pore size distributions for Type 3 titanate as prepared and after ion exchange with the aluminum Keggin ion and then calcined for 1 hour at 300° C. The sorption curves for Type 3-Al-Pillared titanate show the characteristics of layered and possibly pillared material. There is, however, a loss of surface areas and pore volume, apparently due to heating at 300° C.

EXAMPLES

Crystalline titanates in accordance with the present invention were prepared by mixing a titanium-containing compound with an aqueous solution of NaOH, a solution of tetraalkylammonium hydroxide in methanol, $Al(NO_3)_3*9H_2O$, and tetraalkylammonium halides. These chemicals were mixed in an appropriate manner to produce, in most cases, a white precipitate. In some cases, depending on the solution composition, a crystalline titanate formed at room temperature. The slurry mixture was then divided and placed in an oven for heating at a temperature below 180° C. Thereafter, the slurry mixture was rapidly cooled to room temperature to form the crystalline titanates in accordance with the invention.

Example 1

Type 1 crystalline titanates were formed using a $Na_{0.4}T$ composition of hydrous titanium oxide. Thirty grams of tetraisopropyl titanate was reacted with 22 g of 9.59 wt % NaOH in methanol. The product was filtered after about week. The resulting crystals were washed with methanol and stored under methanol-damp conditions.

Example 2

Type 2 crystalline titanates were formed by the following process. 8 g of 10 wt % NaOH was mixed with 7.68 g $H_2O$. 0.75 g of $Al(NO_3)_3 \cdot 9H_2O$ and 2.215 g of tetrapropylammonium chloride were added along with 7.365 g of tetramethylammonium hydroxide (24.71 wt % in methanol). This formed a clear, but colored solution to which 11.36 g of tetraisopropyl titanate was slowly added with stirring. Some precipitate formed. The mixture was heated for 6 days at 89° C. The d-spacing = 1 nm. Sample contained 0.25 wt % Al. Heating for 6 or 12 hours at 148° C. yielded the same d-spacing, and heating for 18 hours at 148° C. produced amorphous powder.

Example 3

Type 3 crystalline titanates were formed by adding 12.5 g of hydrous titanium oxide ($Na_{0.5}T$) and 1.05 g of tetrapentylammonium chloride to 33.5 g of $H_2O$. The pH of the solution was adjusted to at least 13.5, using 10.5 g of 10 wt % NaOH in $H_2O$. The solution was then heated at 168° C. for 19 hours.

Example 4

Type 4a crystalline titanates were formed by adding 22 grams of tetraisopropyl titanate to a mixture of 3.69 g tetramethylammonium hydroxide (24.71% in methanol), 33 g methanol and 4.036 g of tetrapentylammonium chloride. Addition was done slowly while stirring. The resulting solution was initially clear, but a white precipitate appeared shortly after mixing. When heated for 40 hrs at 170° C. the solution produced a crystalline titanate having an interlayer distance of 1.17 nm.

Example 5

Type 4b crystalline titanates were formed by the following process. 7.5 g of tetramethylammonium hydroxide (24.71 wt % in methanol) were added to 27 g methanol. 1.98 g of tetrapentylammonium chloride was then added, followed by 11.36 g tetraisopropyl titanate. The solution remained clear. Heating at 170° C. for 23 hours produced a crystalline titanate with a d-spacing = 1.17 nm.

Example 6

Type 5 crystalline titanate was produced by mixing 7.5 g of tetramethylammonium hydroxide (24.71 wt % in methanol), 18 g $H_2O$ and 1.98 g of tetrapentylammonium chloride together to form a clear solution. 11.36 g of tetraisopropyl titanate were slowly added while stirring. The solution was heated at 150° C. for 5 hours. Acetone was added to the resulting solution to precipitate the crystalline material.

Example 7

A sulfided nickel/molybdenum catalyst was prepared on a crystalline titanate support of the invention using the procedures of Example 1. The prepared catalyst showed high hydrogenation activity.

Example 8

Type 1 crystals were used to prepare a Ni-Mo catalyst by ion exchanging with ammonium heptamolybdate at a pH of 3, followed by rinsing, filtering, and drying. The crystals were reslurried in deionized water and ion exchanged with $Ni(NO_3)_2$ at a pH of 6. The resulting product was rinsed with acetone, dried, and then acidified with HCl to a pH of 3, so as to remove sodium ion. The catalyst was amorphous after calcining at 300° C. The catalytic activity as measured by the hydrogenation of pyrene was significantly greater than catalysts prepared from the amorphous HTO.

Although the present invention has been described in connection with preferred embodiments, it will be appreciated by those skilled in the art that additions, modifications, substitutions and deletions not specifically described may be made without departing from the scope and spirit of the invention defined in the appended claims.

What is claimed is:

1. A process for forming a crystalline catalyst support having a layered structure comprising mixing titanium-containing compound with alkali metal hydroxide, tetraalkylammonium halide, and tetramethylammonium hydroxide at a temperature above 25° C.

2. The process of claim wherein said temperature is in the range of from about 25° C. to about 170° C.

3. The process of claim 1, further comprising ion-exchanging said crystalline catalyst support with a metal or metal oxide.

4. The process of claim 3, wherein said metal is selected from the group consisting of aluminum, nickel, palladium, molybdenum, sulfides of nickel and sulfides of molybdenum.

5. The process of claim 3, wherein said crystalline catalyst support is acidified either before or after said metal or metal oxide is loaded.

6. The process of claim 1, wherein said crystalline catalyst support has ion-exchange properties and a surface area above 50 $m^2/g$.

7. The process of claim 6, wherein said surface area is between 50 and 200 $m^2/g$.

8. The process of claim wherein said crystalline catalyst support has a d-spacing of at least 1.0 nm 9. The process of claim 1, wherein said titanium-containing compound comprises tetraisopropyl titanate.

10. The process of claim 1, wherein said titanium-containing compound comprises titanium oxide.

11. The process of claim 1, wherein said titanium-containing compound comprises titanium alkoxide.

12. The process of claim wherein said crystalline catalyst support contains about 0.2-6 moles of said alkali metal hydroxide per mole of titanium.

13. The process of claim 1, wherein said crystalline catalyst support contains about 0.5-6 moles of said tetraalkylammonium hydroxide per mole of titanium.

14. The process of claim wherein said crystalline catalyst support contains about 0.25 to 0.37 moles of said tetraalkylammonium halide per mole of titanium.

15. A crystalline catalyst support having a layered structure formed by mixing a titanium-containing compound with alkali metal hydroxide, tetraalkylammonium halide, and tetramethylammonium hydroxide at a temperature above 25° C.

16. The crystalline catalyst support of claim 15, wherein said temperature is in the range of from about 25° C. to about 170° C.

17. The crystalline catalyst support of claim 15, wherein said support has ion-exchange properties and a surface area above 50 $m^2/g$.

18. The crystalline catalyst support of claim 17, wherein said surface area is between 50 and 200 $m^2/g$.

19. The crystalline catalyst support of claim 15, wherein said support has a d-spacing of at least 1.0 nm.

20. The crystalline catalyst support of claim 15, wherein said titanium-containing compound comprises tetraisopropyl titanate.

21. The crystalline catalyst support of claim 15, wherein said titanium-containing compound comprises titanium oxide.

22. The crystalline catalyst support of claim 15, wherein said titanium-containing compound comprises titanium alkoxide.

23. The crystalline catalyst support of claim 15, wherein said crystalline catalyst support contains about 0.2-6 moles of said alkali metal hydroxide per mole of titanium.

24. The crystalline catalyst support of claim 15, wherein said crystalline catalyst support contains about 0.5-6 moles of said tetraalkylammonium hydroxide per mole of titanium.

25. The crystalline catalyst support of claim 15, wherein said crystalline catalyst support contains about 0.25 to 0.37 moles of said tetraalkylammonium halide per mole of titanium.

26. A process comprising mixing a titanium-containing compound and an alkali metal hydroxide at a temperature above 25° C., thereby forming a crystalline titanate having a d-spacing of 1.0 nm and a surface area of about 610 $m^2/g$.

27. The process of claim 26, wherein said temperature is in the range of from about 25° C. to about 170° C.

28. The process of claim 26, wherein said crystalline catalyst support has ion-exchange properties and a surface area above 50 $m^2/g$.

29. The process of claim 28, wherein said surface area is between 50 and 200 $m^2/g$.

30. The process of claim 26, wherein said crystalline catalyst support has a d-spacing of at least 1.0 nm.

31. The process of claim 26, wherein said titanium-containing compound comprises tetraisopropyl titanate.

32. The process of claim 26, wherein said titanium-containing compound comprises titanium oxide.

33. The process of claim 26, wherein said titanium-containing compound comprises titanium alkoxide.

34. The process of claim 26, wherein said crystalline catalyst support contains about 0.2-6 moles of said alkali metal hydroxide per mole of titanium.

* * * * *